United States Patent [19]
Cohen et al.

[11] Patent Number: 5,637,464
[45] Date of Patent: Jun. 10, 1997

[54] METHOD OF DETECTING SUB-PPB LEVELS OF OLIGONUCLEOTIDES IN BIOLOGICAL FLUIDS

[75] Inventors: Aharon S. Cohen, Brookline; Alexei Belenky, Newton; Maria Vilenchik, Waban, all of Mass.

[73] Assignee: Hybridon, Inc., Worcester, Mass.

[21] Appl. No.: 465,384

[22] Filed: Jun. 5, 1995

Related U.S. Application Data

[63] Continuation of Ser. No. 187,694, Jan. 26, 1994.

[51] Int. Cl.$^6$ .................................................. C12Q 1/68
[52] U.S. Cl. .................. 435/6; 435/91.1; 435/91.2; 435/810; 436/501; 536/23.1; 536/24.1; 536/24.3; 536/24.31; 536/24.32; 536/24.33; 935/77; 935/78
[58] Field of Search .............................. 435/6, 810, 91.1, 435/91.2; 436/501, 231, 24.1, 24.3–24.33; 935/77, 78

[56] References Cited

U.S. PATENT DOCUMENTS

| | | | |
|---|---|---|---|
| 4,816,571 | 3/1989 | Andrus et al. | 536/27 |
| 4,865,706 | 9/1989 | Karger et al. | 204/182.8 |
| 4,865,707 | 9/1989 | Karger et al. | 204/182.8 |
| 4,883,750 | 11/1989 | Whiteley et al. | 435/6 |
| 4,965,349 | 10/1990 | Woo et al. | 536/27 |
| 5,047,524 | 9/1991 | Andrus et al. | 536/27 |
| 5,112,460 | 5/1992 | Karger et al. | 204/182.8 |
| 5,262,530 | 11/1993 | Andrus et al. | 536/25.31 |
| 5,470,705 | 11/1995 | Grossman et al. | 435/6 |

FOREIGN PATENT DOCUMENTS

| | | |
|---|---|---|
| 0185494 | 6/1986 | European Pat. Off. . |
| 0246864 | 11/1987 | European Pat. Off. . |
| 0318245 | 5/1989 | European Pat. Off. . |
| 0336731 | 10/1989 | European Pat. Off. . |
| 0510824 | 10/1992 | European Pat. Off. . |

OTHER PUBLICATIONS

Agrawal et al., (1991) *Proc. Natl. Acad. Sci. USA* 88:7595–7599.
Rose (1993) *Analytical Chemistry* 65:3545–3549.
Ausebel et al. (1990) *Current Protocols in Molecular Biology* 2:2.2.
Southern (1975) *J. Mol. Biol.* 98:503–517.
Righetti et al. (1977) *J. Chromatog.* 137:171–181.
McBride et al. (1983) *Tetrahedron Lett.* 24:245–248.
Artoni et al. (1984) *Anal. Biochem.* 137:420–428.
Dovichi et al. (1984) *Anal. Chem.* 56:348–354.
Vecchio et al. (1984) *Anal. Biochem.* 137:410–419.
Smith (1985) *Nucl. Acid. Res.* 13:2399–2412.
Wickstrom (1986) *J. Biochem. Biophys. Meth.* 13:97–102.
Zamecnik et al. (1986) *Proc. Natl. Acad. Sci. (US)* 83:4143–4147.
Agrawal et al. (1988) *Proc. Natl. Acad. Sci. (USA)* 85:7079–7083.
Cheng et al. (1988) *Science* 242:562–564.
Cohen et al. (1988) *Proc. Natl. Acad. Sci. (USA)* 85:9660–9663.
Goodchild et al. (1988) *Proc. Natl. Acad. Sci. (USA)* 85:5507–5511.

(List continued on next page.)

*Primary Examiner*—Ardin H. Marschel
*Attorney, Agent, or Firm*—Hale and Dorr

[57] ABSTRACT

Disclosed is a method of detecting a single-stranded target oligonucleotide in a biological fluid. In this method, a biological fluid sample to-be-tested is contacted with helper and primer oligonucleotides, thereby forming a labelled, double-stranded molecule if the sample contains an oligonucleotide which is complementary to the nucleotide sequences of the primer and the helper oligonucleotides. The primer so annealed to the target oligonucleotide is then ligated to the helper annealed to the target oligonucleotide. The presence of the ligation product is being indicative of the presence of the target oligonucleotide in the biological fluid.

11 Claims, 5 Drawing Sheets

OTHER PUBLICATIONS

Landegren et al. (1988) *Science* 241:1077–1080.
Matsukura et al. (1988) *Gene* 72:343–347.
Sarin et al. (1988) *Proc. Natl. Acad. Sci.* (USA) 85:7448–7451.
Agrawal et al. (1989) *Proc. Natl. Acad. Sci.* (USA) 88:7790–7794.
Matsukura et al. (1989) *Proc. Natl. Acad. Sci.* (USA) 86:4244–4248.
Smith (1989) *Am. Biolab.* May:10–20.
Cohen et al. (1990) *J. Chromotog.* 516:49–60.
*Current Protocols in Molecular Biology* (Ausubel et al., eds.) John Wiley & Sons, New York (1990) 2:2.2.
Swerdlow et al. (1990) *Nucl. Acids Res.* 18:1415–1418.
Uhlmann et al. 1990 *Chem. Rev.* 90:543–583.
Agrawal in *Prospects for Antisense Nucleic Acid Therapy for Cancer and AIDS*, (Wickstrom, ed.) Liss, New York, (1991) pp. 143–158.
Agrawal et al. (1991) *Proc. Natl. Acad. Sci.* (USA) 88:7595–7599.
Matsukura et al. in *Prospects for Antisense Nucleic Acid Therapy of Cancern and AIDS*, Wiley–Liss, Inc. (1991) pp. 159–178.
Vickers et al. (1991) *Nucleic Acids Res.* (USA) 19:3359–3368.
Agrawal et al. (1992) *Trends in Biotechnology* 10:152–158.
Agrawal et al. in *Gene Regulation: Biology of Antisense RNA and DNA* (Erickson and Izant, eds.) Raven Press Ltd., New York (1992) pp. 273–283).
Pompon et al. (1992) *Biochem. Pharm.* 43:1769–1775.
Bourque et al. (1993) *J. Chromotog.* 617:43–49.
Cohen et al. (1993) *J. Chromotog.* 638:293–301.
Cohen et al. (1993) *Trends Anal. Chem.* 12:195–202.
Lim et al. (1981) *IEEE Transactions on Nuclear Science*, vol. NS-28, No. 1, pp. 152–160.

METHOD OF DETECTING SUB-PPB LEVELS OF OLIGONUCLEOTIDES IN BIOLOGICAL FLUIDS

CROSS-REFERENCE TO RELATED APPLICATION

This is a continuation application of patent application Ser. No. (08/187,694), entitled "METHOD OF DETECTING SUB-PPB LEVELS OF OLIGONUCLEOTIDES IN BIOLOGICAL FLUIDS", filed on Jan. 26, 1994, and assigned to the present assignees.

FIELD OF THE INVENTION

This invention relates to the detection of nucleic acids. More particularly, this invention relates to the detection and quantitation of low levels of specific oligonucleotides present in biological fluids.

BACKGROUND OF THE INVENTION

Detection of specific nucleic acid sequences present in cells is generally known in the art. Southern (*J. Mol. Biol.* (1975) 98: 503–517) teaches the detection of specific sequences among DNA fragments separated by gel electrophoresis using "blotting" or transfer of the DNA fragments to a membrane, followed by hybridization of denatured DNA fragments with a radioactive probe and autoradiography. This procedure has also been extended to the detection of RNA molecules extracted from cells or tissues. More recently, faster and quantitative "dot-blotting" procedures have been developed for rapid detection of DNA or RNA from tissues or cells.

Recently, considerable interest has been generated in the development of synthetic oligonucleotides as therapeutic or gene expression modulating agents in the so-called antisense approach. These agents, called antisense oligonucleotides, bind to a target single-stranded nucleic acid molecule according to the Watson-Crick or the Hoogstein rule of base pairing, and in doing so, disrupt the function of the target by one of several mechanisms: by preventing the binding of factors required for normal translation or transcription; in the case of an mRNA target, by triggering the enzymatic destruction of the messenger by RNase H; or by destroying the target via reactive groups attached directly to the antisense oligonucleotide.

Antisense oligodeoxynucleotides have been designed to specifically inhibit the expression of HIV-1 and other viruses (see, e.g., Agrawal (1992) *Trends in Biotechnology* 10: 152–158; Agrawal et al. in *Gene Regulation: Biology of Antisense RNA and DNA* (Erickson and Izant, eds.) Raven Press Ltd., New York (1992) pp. 273–283); Matsukura et al. in *Prospects for Antisense Nucleic Acid Therapy of Cancer and AIDS*, Wiley-Liss, Inc. (1992) pp. 159–178; and Agrawal (1991) in *Prospects for Antisense Nucleic Acid Therapy for Cancer and AIDS*, (Wickstrom, ed. ) Liss, New York, pp. 145–148). For example, it has been shown that antisense oligonucleotides having unmodified phosphodiester or modified internucleoside bonds and sequences complementary to portions of genomic HIV-1 ribonucleic acid (RNA) inhibit viral replication in early infected cells (Zamecnik et al. (1986) *Proc. Natl. Acad. Sci.* (USA) 83: 4143–4147; Goodchild et al. (1988) *Proc. Natl. Acad. Sci* (USA) 85: 5507–5511).

However, molecules with unmodified phosphodiester bonds are less able to inhibit viral replication in chronically infected cells (Agrawal et al. (*1989*) *Proc. Natl. Acad. Sci.* (USA) 86: 7790–7794), mainly because of their nuclease susceptibility (Wickstrom (1986) *J. Biochem. Biophys. Meth.* 13: 97–102). Therefore, chemically modified, nuclease-resistant analogs have been developed which are effective in inhibiting HIV-1 replication in tissue cultures (Sarin et al. (1988) *Proc. Natl Acad. Sci.* (USA) 85: 7448–7451; Agrawal et al. (1988) *Proc. Natl. Acad. Sci.* (USA) 85: 7079–7083; Matsukura et al. (1988) *Gene* 72: 343–347). These analogs include oligonucleotides with nuclease-resistant phosphorothioate internucleotide linkages shown to inhibit HIV-1 replication in both acute infection (Agrawal et al. (1989) *Proc. Natl. Acad. Sci* (USA) 86: 7790–7794) and in chronically infected cell lines (Agrawal et al. (1991) in *Gene Regulation: Biology of Antisense RNA*, (Erickson et al., eds.) Raven Press, New York, pp. 273–284; Vickers et al. (1991) *Nucleic Acids Res.* 19: 3359–3368; Matsukura et al. (1989) *Proc. Natl. Acad. Sci.* (USA) 86: 4244–4248; Agrawal et al. (1988) *Proc. Natl Acad. Sci.* (USA) 85: 7079–7083).

For an antisense therapeutic approach to be effective, oligonucleotides must be introduced into a subject and must reach the specific tissues to be treated. Consequently, analytical methods are needed to detect oligonucleotides in body fluids or tissues.

Temsamani et al. (U.S. patent application Ser. No. 08/002,786) developed a method of extracting oligonucleotides which had been proteolytically digested from body fluid or tissue samples. Total nucleic acids are precipitated from the extracted samples and transferred to a hybridization membrane where they are hybridized to a labelled oligonucleotide that is complementary to the oligonucleotide that was administered to the subject. Presence of the hybridized, labelled oligonucleotide is then detected by standard procedures.

Radiolabelled oligonucleotides have been administered to animal models and their distribution within body fluids and tissues has been assessed by extraction of the oligonucleotides followed by autoradiography (see Agrawal et al. (1991) *Proc. Natl. Acad. Sci.* (USA) 88: 7595–7599). As a practical matter, however, these methods have not been exercised in human patients.

Unfortunately, the various techniques for detecting specific unlabelled nucleic acid sequences present in body fluids or tissues has thus far only been extended to polynucleotides such as large DNA or RNA molecules. Due to the small size of antisense oligonucleotides, special problems relating to nonspecific binding or background, as well as to absence of binding, nondetection, or false negatives exist. Thus, there remains a need to develop procedures for the detection of specific synthetic oligonucleotide sequences present in biological fluids such as body fluids and tissues.

Bioavailability and pharmacokinetic measurements of metabolites in samples of blood, tissue, urine, and other biological fluids, have been made using detection methods involving autoradiography (Agrawal et al. (1991) *Proc. Natl. Acad. Sci.* (USA) 88: 7595). In addition, detection of oligonucleotides has been accomplished by UV detection of a natural chromophore in the molecule. However, quantitative detection of oligonucleotides by UV is limited to concentrations of 50–100 parts per billion (ppb) or about $10^{-8}$M in the sample vials at best. When more sensitive detection is required, radioactive and laser induced fluorescence (LIF) are the methods of choice. For example, laser-induced fluorescence has the capacity to detect small numbers of rhodamine molecules in an aqueous flowing solution (Dovichi et al. (1984) *Anal. Chem.* 56: 348–354).

Since neither radioactive nor fluorescent labelled oligonucleotides are used in humans, direct determination of oligonucleotide analogs in biological fluids at very low concentrations (sub-ppb) is currently impossible. A combination of capillary gel electrophoresis and laser-induced fluorescence has been used to measure DNA sequence reaction products (see, e.g., Cohen et al. (1990) *J. Chromatogr.* 516: 49–60; Swerdlow et al. (1990) *Nucl. Acids Res.* 18: 1415–1418) and derivatized amino acids (Cheng et al. (1988) *Science* 242: 562–564). However, these methods are unable to detect minute levels of small oligonucleotides such as those useful in antisense therapy which are in their native form.

Thus, at present there remains a need for methods of detecting and quantitating very low levels of small oligonucleotides in biological fluids.

SUMMARY OF THE INVENTION

An analytical method has been developed which enables the detection of minute (as little as sub parts per billion (sub ppb)) quantities of single-stranded oligonucleotides in a biological fluid. The method is fast, accurate, and less laborious than the alternative radioactive bioassay. Thus, the method has a unique advantage in the antisense field, where modified drug molecules are under drug regulatory evaluation and where analytical information is badly needed.

The biological fluid suspected of containing a target oligonucleotide of interest (i.e., the biological fluid-to-be-tested) is contacted with a primer molecule and a helper molecule. The primer is a single-stranded oligonucleotide consisting of at least four, but preferably at least eight, covalently linked nucleotides but less than the number of nucleotides in a target oligonucleotide. The primer is complementary to a portion of the target oligonucleotide.

As used herein, the term "oligonucleotide" includes polymers of three or more ribonucleotide and/or deoxyribonucleotide monomers connected together or linked by at least one 5' to 3' internucleotide linkage.

A fluorescent label is covalently linked to at least one of the primer nucleotides which, in preferred embodiments of the invention, the label is excitable in the UV or visible range and fluoresces in the visible range.

The helper, like the primer, is a single-stranded oligonucleotide. It must have at least three covalently linked nucleotides, and in one embodiment of the invention, has from about 3 to about 100 nucleotides. In another embodiment, the helper has at least 5 nucleotides, which, in yet another embodiment, includes at least two nucleotides of which are complementary to the target molecule, and either having a remainder extending beyond the 3' end of the target oligonucleotide or ending before the 3' end of the target oligonucleotide to which it has annealed.

The conditions under which the biological fluid is contacted must be conducive for the annealing of the primer and the helper to a complementary, single-stranded oligonucleotide, such as the target molecule if it is present in the biological fluid sample. In one aspect of the invention, such conditions include contact at from about 4° C. to 90° C. in the presence of from about 0.05M to 2.0M salt, the salt comprising an alkali metal or an alkaline earth metal. Some preferred salts include $MgCl_2$, NaCl, and LiBr.

In a preferred aspect of the invention, at least about 100 parts primer and at least about 100 parts helper are mixed with a biological sample presumed to contain about 1 to 10 parts target oligonucleotide. Given that the level of detection by this method using LIF is 0.1 ppb, 10 ppb primer and 10 ppb helper are preferably the smallest amounts that are used to contact the biological fluid sample. A labelled, double-stranded molecule will form if the sample contains the target oligonucleotide, and if that target molecule has a nucleotide sequence complementary to the nucleotide sequences of the primer and the helper.

Following contact, the primer annealed to the target oligonucleotide is ligated to the helper annealed to the same target oligonucleotide, thereby forming a labelled, single-stranded ligation product which is hybridized to the target molecule. A preferred ligation method is the enzymatic joining of the primer and the helper using, for example, T4-DNA ligase, (Taq) DNA ligase, or *E. coli* DNA ligase.

Following ligation, the ligation product is separated from the primer, helper, and target oligonucleotides. In a preferred embodiment separation is accomplished by high performance capillary electrophoresis (HPCE) under denaturing conditions. The labelled ligation product is then detected, the presence of the product being indicative of the presence of the target oligonucleotide in the biological fluid. In preferred aspects of the invention, detection is accomplished by UV absorption or laser-induced fluorescence (LIF). In others, the relative concentration or number of molecules of target oligonucleotide in the biological fluid is determined by quantifying the detected ligation product.

The target oligonucleotides that can be identified and analyzed by this method include oligonucleotides and analogs of oligonucleotides or modified oligonucleotides containing nucleotides selected from the group consisting of ribonucleotides, deoxyribonucleotides, modified ribonucleotides, modified deoxyribonucleotides, and mixtures thereof.

As used herein, a "mononucleotide analog" or "modified mononucleotide" is a base, including purines and pyrimidines, or modifications thereof, attached to the 1' end of the deoxyribose or ribose sugar, or modifications thereof, which is attached at its 5' position to a phosphate group. Also included as a mononucleotide analog are cyclic mononucleotides.

The terms "modified oligonucleotide" and "oligonucleotide analog," are meant to encompass a molecule of ribonucleotides or deoxyribonucleotides at least two of which are covalently linked via a synthetic linkage. A "synthetic internucleotide linkage" is a linkage other than a phosphodiester between the 5' end of one nucleotide and the 3' end of another nucleotide in which the 5' nucleotide phosphate has been replaced with any number of chemical groups. Preferable synthetic linkages include alkylphosphonates, phosphorothioates, phosphorodithioates, alkylphosphonothioates, phosphoramidates, phosphate esters, carbamates, carbonates, phosphate triesters, acetamidate, and carboxymethyl esters.

The terms "modified oligonucleotide" and "oligonucleotide analog" also encompass oligonucleotides with a modified base and/or sugar. For example, a 3', 5'-substituted oligonucleotide is a modified oligonucleotide having a sugar which, at both its 3' and 5' positions is attached to a chemical group other than a hydroxyl group (at its 3' position) and other than a phosphate group (at its 5' position). A modified oligonucleotide may also be a capped species. Also encompassed by these terms are unoxidized or partially oxidized oligonucleotides having a substitution in one nonbridging oxygen per nucleotide in the molecule.

Oligonucleotide analogs also include synthetic oligonucleotides. "Synthetic oligonucleotides" encompass polymers of 3' to 5' -linked ribonucleosides, 2'-modified ribonucleosides and/or deoxyribonucleosides having only as many nucleosides as are conveniently chemically synthesized (i.e., up to about 100). Also encompassed are those oligonucleotides having nuclease resistance-conferring bulky substituents at their 3' and/or 5' end(s) and/or various other structural modifications not found in vivo without human intervention.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1A:
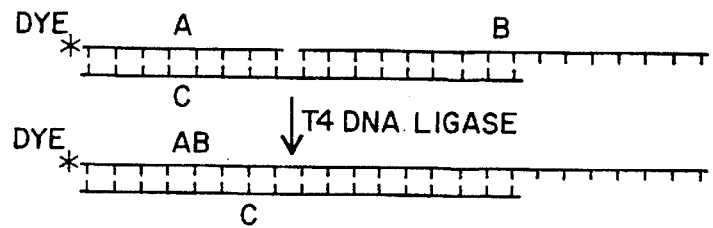
FIG. 1A is a diagrammatic representation of the method of the invention.

The patent and scientific literature referred to herein establishes the knowledge that is available to those with skill in the art. The issued U.S. patent and allowed applications cited herein are hereby incorporated by reference.

This invention provides a method of detecting a target oligonucleotide which may be present at as little as sub-ppb levels in a biological fluid. The method is indirect in that the target oligonucleotide, itself, is not measured, but rather a product which is produced as the result of the presence of the target oligonucleotide. The method requires neither radioactive nor fluorescent labels to be administered to live subjects, but instead, involves the application of a fluorescently labelled molecule to a sample of the biological fluid which potentially contains the target oligonucleotide complementary sequence.

In this method, a labelled primer oligonucleotide and an unlabelled helper oligonucleotide are put in contact with a biological fluid sample to be tested for the presence of a target molecule. Two examples of the method are shown schematically in FIGS. 1A and 1B, where "A" is a fluorescently labelled primer; "B" is a helper; "C" is target oligonucleotide; and "AB" is the labelled ligation product.

The primer is a short oligonucleotide to which a fluorescent label or fluorophore is attached. It includes at least six ribonucleotide and/or deoxyribonucleotide monomers connected together or linked by at least one 5' to 3' internucleotide linkage. These internucleotide linkages may be any known in the art, such as alkylphosphonates, phosphorothioates, phosphorodithioates, alkylphosphonothioates, phosphoramidates, phosphate esters, carbamates, carbonates, phosphate triesters, acetamidate, and carboxymethyl esters (Uhlmann et al. (1990) *Chem. Rev.* 90: 543–583). It is required that the primer have a nucleotide sequence that is complementary to a portion of the target molecule. This portion must be less than the entire target molecule as the helper molecule, to which the primer will be ligated, must also hybridize in part to the target molecule.

At least one molecule of fluorescent label is attached to the primer. This label is excitable in the UV or visible wavelength range, and fluoresces in the visible range. Such labels include fluorescein, or the N-succinimide ester or other derivatives thereof, such as called "JOE" (Applied Biosystems, Foster City, Calif.), "FITC" (Applied Biosystems, Foster City, Calif.), and "FAM" (Applied Biosystems, Foster City, Calif.) and rhodamine, or derivatives thereof, such as tetramethylrhodamine ("TAMARA") (Applied Biosystems, Foster City, Calif.) and "Texas Red" or "ROX" (Smith (1985) *Nucl. Acid. Res.* 13: 2399–2412) (Applied Biosystems, Foster City, Calif.). These labels can be covalently attached to the primer, for example, by using chemical DNA or RNA synthesis as described by Smith (*Am. Biolab.* (1989) May: 11–20) or by other methods which will not interfere with the ability of the primer to hybridize to the target molecule or to be ligated to the helper oligonucleotide. An example of one such method includes covalently attaching an amino group onto the dye and then linking the amino group 5' end of oligonucleotide (Smith (1985) *Nucl. Acid. Res.* 13: 2399–2412).

Figure 1B:
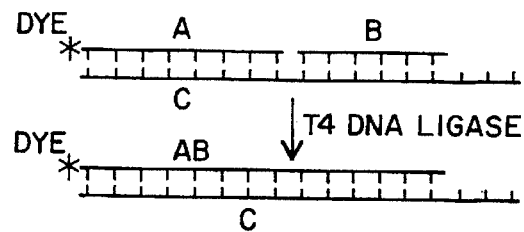
FIG. 1B is a diagrammatic representation of another embodiment of the method of the invention.

The helper is an oligonucleotide consisting of three or more, and preferably 4 to 50 ribonucleotides and/or deoxyribonucleotides and/or analogs thereof linked via any internucleotide linkage known in the art, such as those described above which link primer nucleotides. The nucleotide sequence of the helper is at least complementary to a portion of the nucleic acid sequence of the target molecule adjacent the portion which is complementary to the primer (see FIG. 1). Actually, only two nucleotides, but preferably 3 or more nucleotides of the helper need be complementary to the target molecule. The helper may have a sequence which extends beyond the 3' end of target oligonucleotide (FIG. 1A). Alternatively, the helper may have a sequence which ends before the 3'-end of the target oligonucleotide (FIG. 1B).

The target molecule can be any oligonucleotide found naturally in vivo or an analog thereof. Thus, the target molecule can contain at least one phosphodiester internucleotide linkage as is found in endogenous RNA and DNA, or it can be an oligonucleotide analog or modified oligonucleotide. The target molecule can also be an oligonucleotide which has been added to the biological fluid sample or to the organism from which the biological fluid sample is obtained.

In the method of the invention, a biological fluid sample to-be-tested is put in contact with the primer and helper oligonucleotides The biological fluid that can be tested by this method includes any sample from an organism, culture, or tissue which has been treated with an oligonucleotide analog or other target oligonucleotide for any number of purposes, including antisense or gene therapy. Examples of biological fluids include any body fluid such as serum, plasma, urine, semen, seminal fluid, lacrimal secretions, sweat, mucous secretions, cerebrospinal fluid, synovial fluid, and saliva. Such fluids are sampled from the body by normal medical and surgical procedures. Other biological fluids which also can be monitored by this method include the extract of a cell such as a plant, bacterial, animal, or fungal cell or of a tissue. Cell and tissue extracts may be prepared according to any known method including, for example, mechanical or enzymatic shearing or disruption of cell membranes (and walls in the case of plants and fungal spores), followed by separation of the extract from the particular matter via, e.g., differential centrifugation (see, e.g., *Current Protocols in Mol. Biol.* (Ausubel et al., eds.) John Wiley & Sons, New York (1990) 2: 2.2).

The biological sample and primer and helper oligonucleotides are mixed under conditions that are conducive for the annealing of single-stranded species to a complementary, single-stranded oligonucleotide. These conditions include contact at a temperature of from about 4° C. to 90° C., but preferably at room temperature (i.e., 19° C. to 25° C.). In addition, contact is carried out in the presence of Tris-HCl buffer and from about 0.05M to 2.0M salt containing an alkali metal or an alkaline earth metal. Representative useful salts include NaCl, $MgCl_2$, and LiBr.

The concentrations of primer and helper used are selected so as to push the equilibrium hybridization/dissociation reaction toward hybridization: at least about 100 parts primer and at least about 100 parts helper are used to detect about 1 to 10 part(s) target oligonucleotide. For example, to determine if the biological fluid contains the target molecule, the assumption is that there is 0.1 ppb present in the sample (i.e., the lowest level of detection possible by LIF, the most sensitive of detectors). To detect 0.1 ppb target oligonucleotide, at least 10 ppb each primer and helper are required to push the reaction towards hybridization. If there is greater than 0.1 ppb target molecule present in the fluid, the amounts of primer and helper can be reduced so as not to overload the high performance capillary and so that the tracings of the labelled species on the resulting electropherogram are on scale.

Successful hybridization results in a labelled, double-stranded molecule having one strand consisting of two unlinked fragments: the labelled primer and the unlabelled helper. Linkage of these annealed fragments to yield a single-stranded ligation product is accomplished enzymatically using T4 DNA or RNA ligase, (Taq) DNA ligase, *E. coli* DNA ligase, or other enzymes capable of linking the 5' end of the hybridized primer to the 3' end of the hybridized helper. Ligation may be conducted at 19° C. to 37° C. in the presence of a buffer containing, for example, 500 mM Tris, 100 mM $MgCl_2$, 100 mM DTT, 100 mM ATP, 15 µg/ml BSA, 10–50 units T4 ligase (U.S. Biolab protocol, U.S. Biolab, Cleveland, Ohio).

The double-stranded molecule formed upon the hybridization of the primer and the helper may also have a single-stranded region which represents that portion of the helper which is not complementary to the target molecule, e.g., a sequence which extends beyond the 3' end of the target molecule. Such a region does not affect the ability of the present claimed method to detect target molecule.

Once formed, the ligation product is analyzed by HPCE under denaturing conditions, during which the separation of ligation product, primer, helper, and target oligonucleotides was achieved by high performance capillary gel electrophoresis (HPCE) under denaturing conditions (see, e.g., Cohen et al. (1993) *Trends Anal. Chem.* 12: 195–202; Bourque et al. (1993) *J. Chromatog.* 617: 43–49; Cohen et al. (1990) *J. Chromatog.* 516: 49–60, and Cohen et al. *Proc. Natl. Acad. Sci.* (1988) 85: 9660–9663.

The substrate used to separate oligonucleotides by HPCE may be any substrate known in the art to be useful for such a purpose. For example, unmodified and modified mononucleotides and oligonucleotides can be separated by HPCE on a substrate including at least 12% (weight:volume) polymer in at least 5M urea and at least 14% (volume:volume) organic solvent, as described in copending patent application Ser. No. 08/178,660. Charged oligonucleotides can be separated on a strong or weak anion exchange resin, as described in copending patent application Ser. No. 08/153,365.

The substrate is placed in a capillary or tube before polymerization. In the case of acrylamide, polymerization may be achieved by adding ammonium persulfate and a free radical catalyst such as N,N,N',N'-tetramethylene-diamine (TEMED) to the acrylamide solution just before it is placed in the capillary. Alternatively, photopolymerization or other modes of polymerization may be used depending on the type of polymer present in the substrate. A useful capillary is a microcapillary column (25 to 200 µm inner diameter) made of fused silica, as described in U.S. Pat. Nos. 4,865,706 and 5,112,460, herein incorporated by reference. Alternatively, a 20×2 mm inner diameter stainless steel guard column hand packed with an ionic exchange resin of choice can be used. In particular, a capillary of 75 µm gives better heat transport by one or two orders of magnitude than conventional electrophoresis. Consequently, very high potentials can be used to produce ultra high efficiency (Cheng et al. (1988) *Science* 242: 262–264). The capillary gel is run at at least 200 V/cm and preferably at from 400 V/cm to 800 V/cm. A power supply is used to generate the potential across the capillary.

Once the ligation product has been separated from the other oligonucleotide species, it is detected and quantitated. Detection of the fluorescently labelled product is indicative of the presence of the target oligonucleotide, and can be achieved by UV absorption if the target oligonucleotide is present in the biological fluid at at least 0.5 ppm. For example, the ligation product can be detected via UV absorbance at 260–270 nm using a spectrophotometer or other variable wavelength detector. The detector response is calibrated using known concentrations of analog or oligonucleotide (spiked) in the biological fluid being measured.

If there is less than 0.5 ppm but greater than or equal to 0.1 ppb target molecule present, LIF can be used. Only fluorescently labelled oligonucleotides will be detected, as natural DNA and RNA do not have a chromophore detectable by LIF at 500 nm. Therefore, only two peaks are expected in the resulting electropherogram: the earlier one representing excess labelled primer and the later one representing the heavier ligation product. The ligation reaction is very specific and therefore only one kind of oligonucleotide is "fished" out. The ratio of ligation product to target oligonucleotide is 1:1, and therefore that ratio is independent of target molecule concentration.

For example, the method of the invention can be performed as follows: A fluorescent 5'-end labelled 13 mer phosphodiester-linked primer (SEQ ID NO:2) and a 12 mer (SEQ ID NO:3) or 33 mer (SEQ ID NO:4) phosphodiester-linked DNA helper, both having complementary sequences to a 25 mer single-stranded DNA the antisense phosphorothioate analog (SEQ ID NO:1) are added to a fluid sample containing the 25 mer as the template target molecule.

Figure 2A:
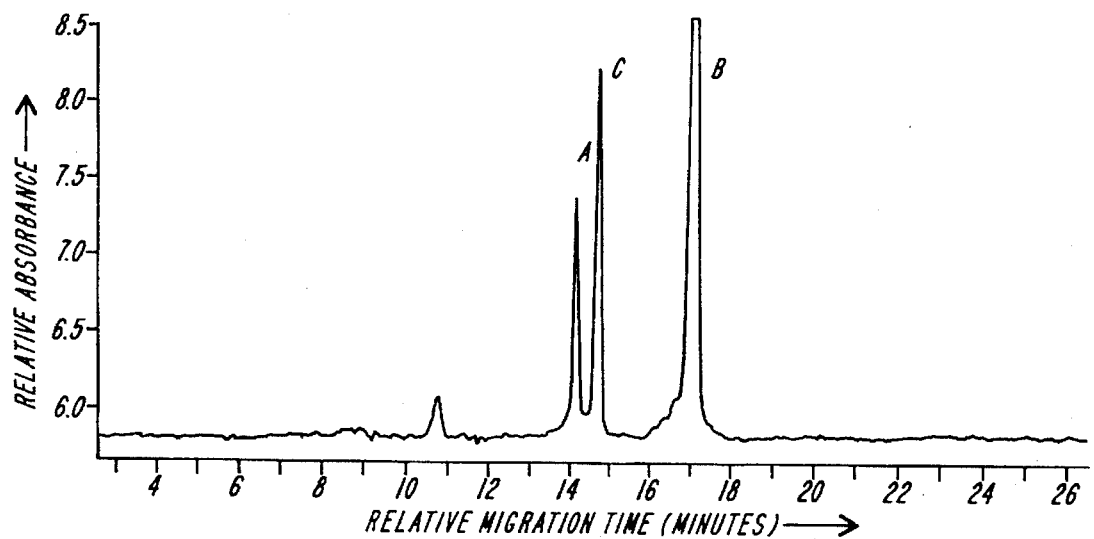
FIG. 2A is a UV electropherogram showing the detection and separation of the primer (A) (100 ppb), helper (B) (500 ppb), and target (C) (50 ppb) oligonucleotides before ligation.

FIG. 2A is an electropherogram which is obtained before ligation. The oligonucleotides are separated in a 12 cm capillary containing a HPCE substrate of 11% T acrylamide, 32% (volume:volume) formamide, 6M urea, and 2×TBE buffer. The gel is run at 400 V/cm, as described in copending patent application Ser. No. 08/032,856. As expected, the three individual components are well separated and identified. The labelled 13 mer primer (SEQ ID NO:2) has the highest mobility and the 33 mer helper (SEQ ID NO:4) has the lowest mobility. The peak after the helper (b, c) is a side effect of ligation (i.e., ligation at the 5' end of the helper with ATP which is in excess in the ligation mixture).

Figure 2B:
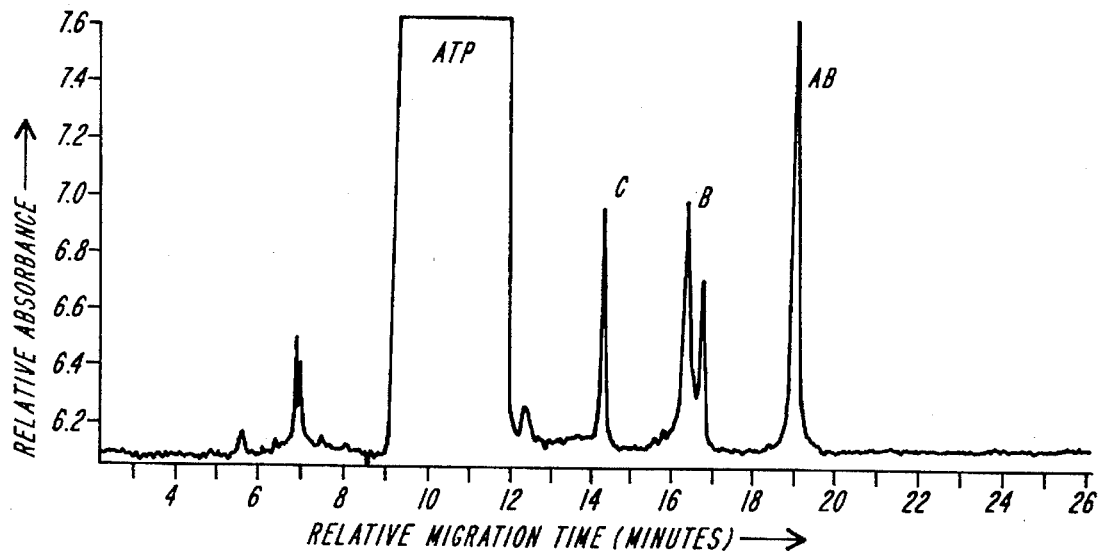
FIG. 2B is a UV electropherogram showing the detection and separation of primer (A) (100 ppb), helper (B) (500 ppb), and target (C) (50 ppb) oligonucleotides after ligation.
Figure 2C:
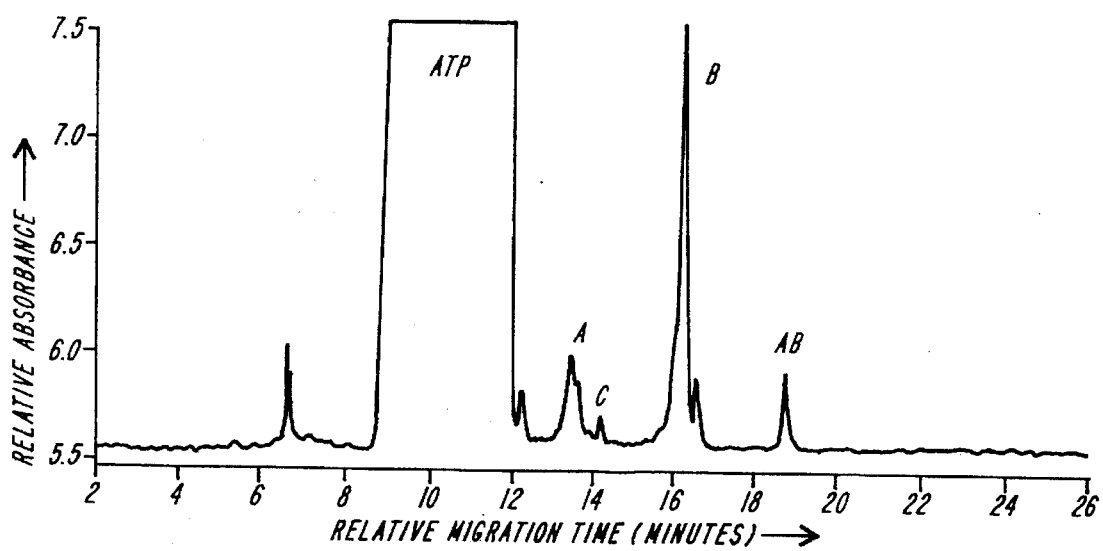
FIG. 2C is a UV electropherogram showing the detection and separation of primer (A) (100 ppb), helper (B) (500 ppb), and target (C) (10 ppb) oligonucleotides after ligation.

After the ligation step, the electropherograms shown in FIGS. 2B and 2C are more complicated. The overloaded peak is the excess of ATP (needed for the energy cycle). The primer peak (A) is missing as it is probably consumed in the ligation reaction due to the excess of target oligonucleotide (C). The helper (B) is partially consumed and split due to ligation of an ATP to the helper. The latest migrating peak is a 46 mer ligation product (AB) (SEQ ID NO:5) (13 mer primer+33 mer helper=46 mer). If the presence of target oligonucleotide (C) in the ligation mixture is 5-fold lower, the disappearance of the target oligonucleotide (C), excess of the primer (A), large excess of the helper (B), and much lower amounts of the ligation product (AB) are observed as shown in FIG. 2C.

Figure 3:
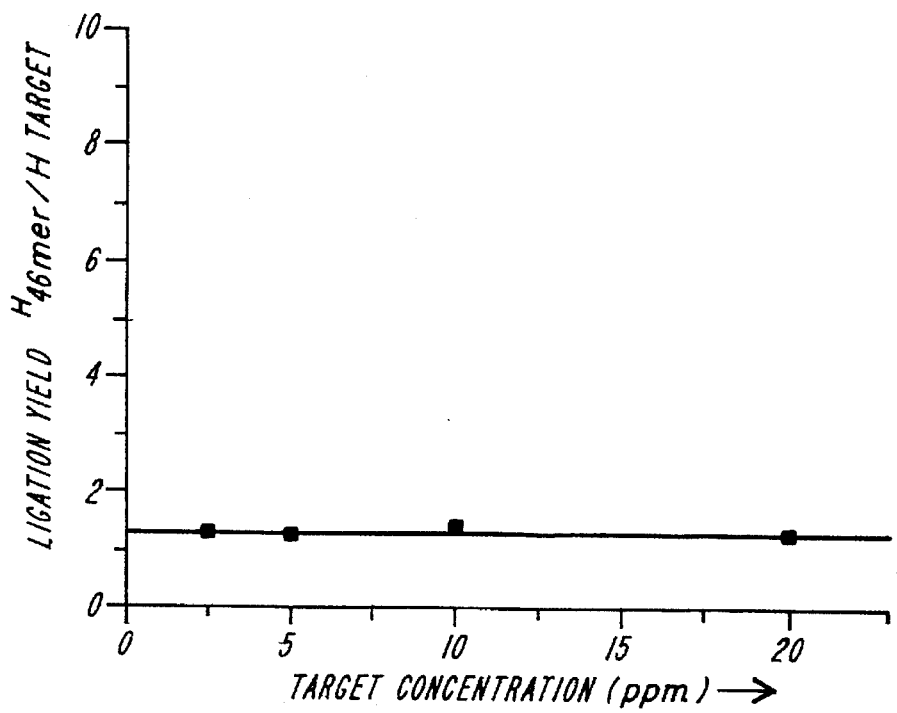
FIG. 3 is a graphic representation of the lack of dependency of the ligation yield on the concentration of target oligonucleotides.

The validity of the indirect determination approach is demonstrated in FIG. 3. The normalized peak height of the ligation product is plotted against target oligonucleotide concentration. A linear behavior with a slope equal to zero is obtained. This behavior indicates that the ligation product to target oligonucleotide molar ratio in the test samples is 1:1, and thus is independent of target oligonucleotide concentration. This is crucial for indirect quantitative analysis since it demonstrates that the hybridization reaction is dominated by the template which is the target oligonucleotide.

The ability of the method to quantitate target molecules in complex biological fluids such as plasma is demonstrated in the LIF electropherograms shown in FIGS. 4A–4F. Although plasma proteins are known to bind non-selectively to oligonucleotide analogs such as phosphorothioates, it has been determined that the recovery of analog from serum is as good as the recovery of analog from buffer using the solid state extraction method of Cohen et al. (patent application Ser. No. 08/153,365). Thus, quantitation by the present method is possible. More specifically, these figures illustrate the separation of the ligation product (AB) from the primer (A) by HPCE coupled with a LIF detector. In these studies, a 25 mer (SEQ ID NO:1) is used as internal standard. The primer (A) is always in excess, the concentration of the internal standard is always 5 ppb, and presence of target oligonucleotide (C) varies between 0.5 ppb to 20 ppb.

Figure 5:
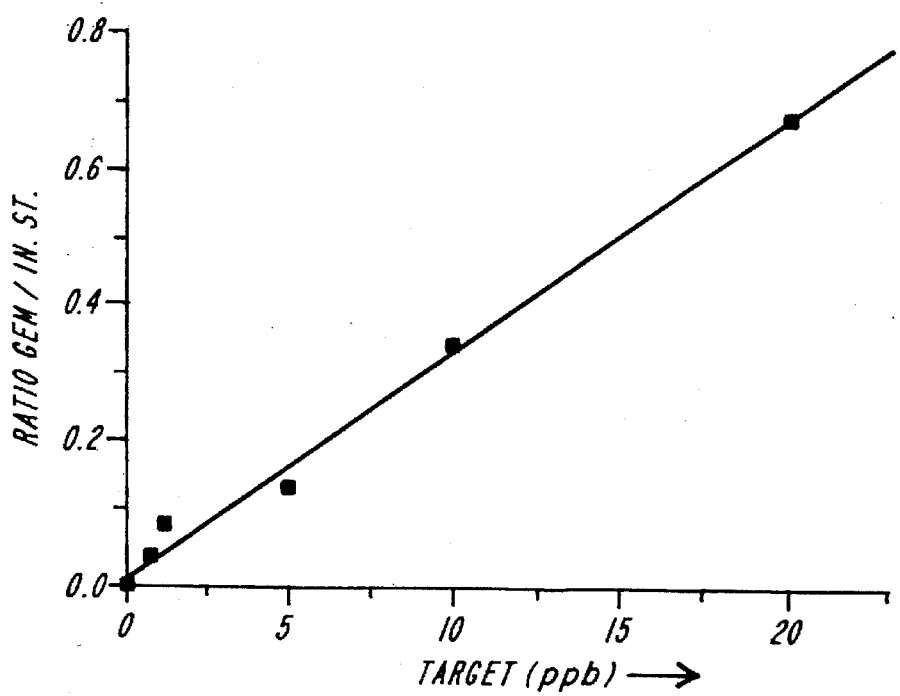
FIG. 5 is a calibration curve for the LIF determination of target oligonucleotide concentration in serum samples based on the data shown in FIGS. 4A-4F: normalized analytical signals versus target oligonucleotide concentrations.
Figure 4A:
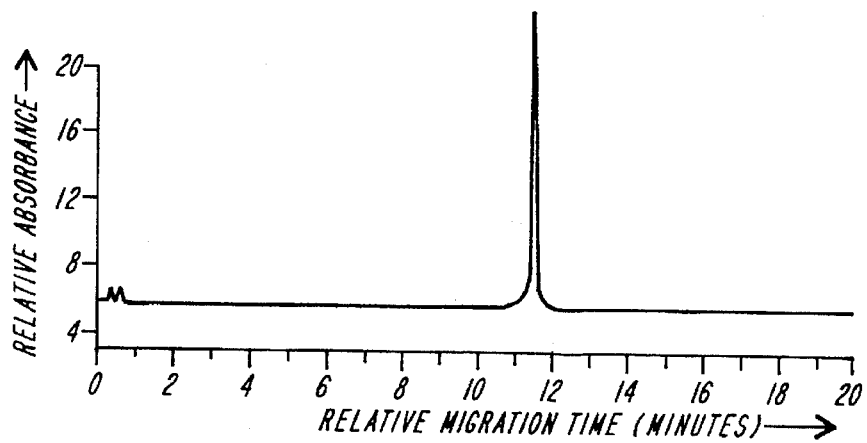
FIG. 4A is an LIF electropherogram of internal standard (5 ppb)
Figure 4B:
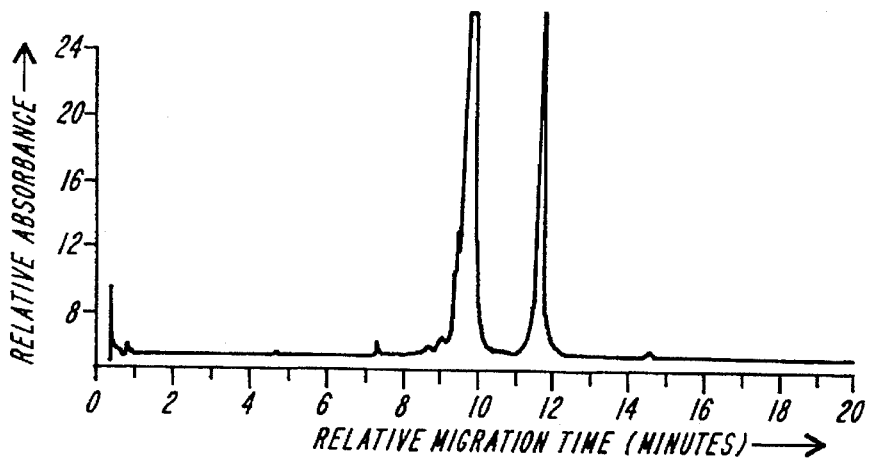
FIG. 4B is an LIF electropherogram of a mixture containing primer, internal standard, and target ppb) oligonucleotide (0.5 ppb) after ligation.
Figure 4C:
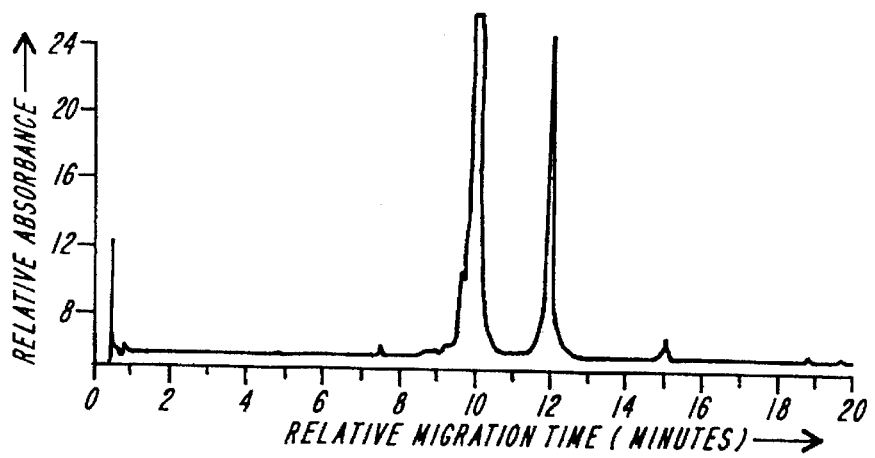
FIG. 4C is an LIF electropherogram of a mixture containing primer, internal standard, and target oligonucleotide (1.0 ppb) after ligation.
Figure 4D:
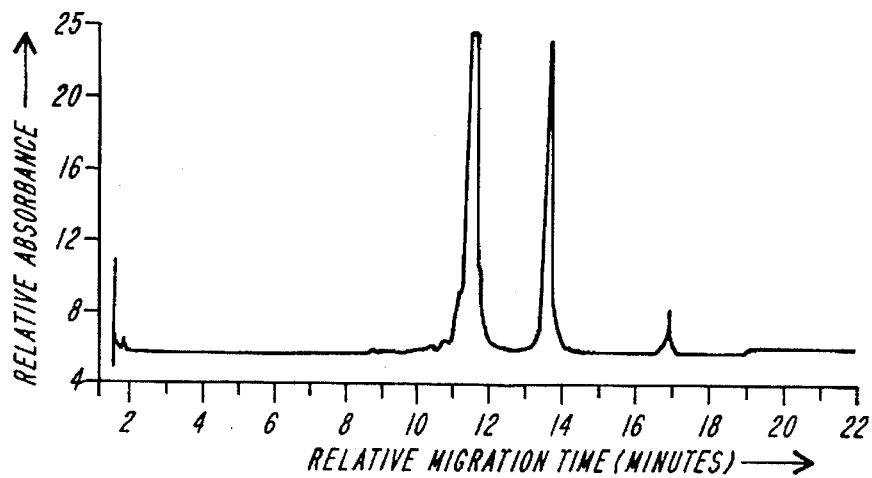
FIG. 4D is an LIF electropherogram of the mixture containing primer, internal standard, and target oligonucleotide (5.0 ppb) after ligation.
Figure 4E:
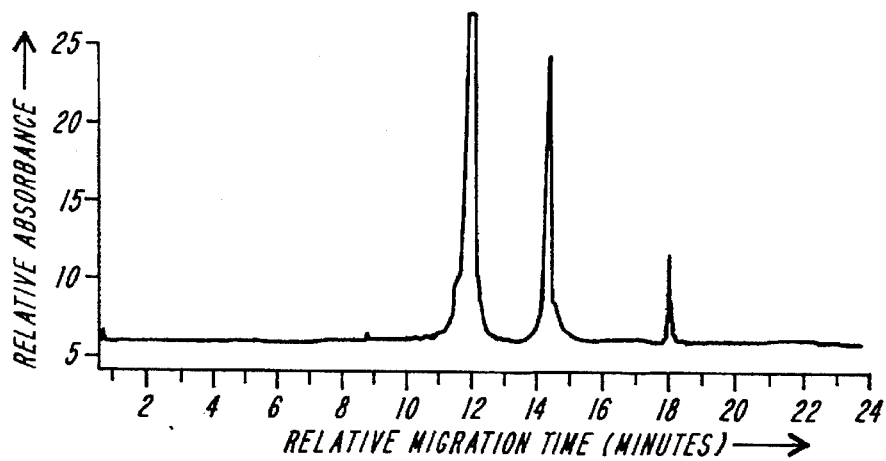
FIG. 4E is an LIF electropherogram of a mixture containing primer, internal standard, and target oligonucleotide (10 ppb) after ligation.
Figure 4F:
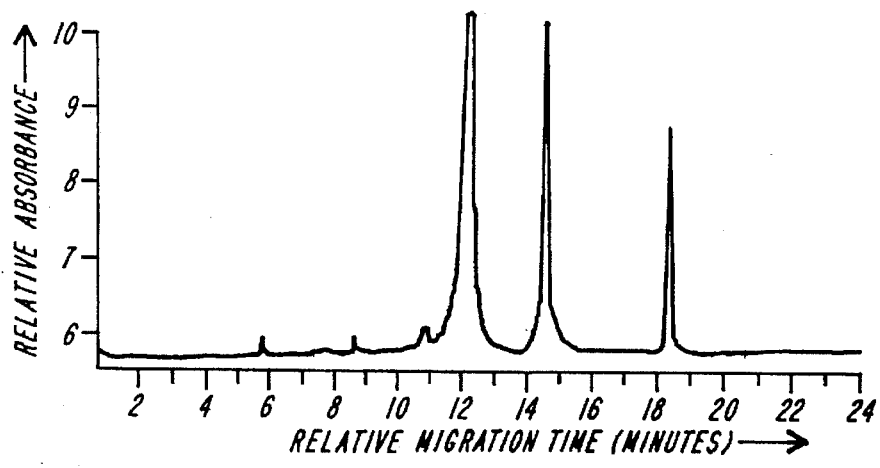
FIG. 4F is an LIF electropherogram of a mixture containing primer, internal standard, and target oligonucleotide (20 ppb) after ligation.

Since the ligation product (AB) corresponds directly to the target oligonucleotide concentration in the sample, a calibration curve can be plotted. The results from FIGS. 4A–4F are used to produce such a calibration curve as shown in FIG. 5. The height of the peak of the target oligonucleotide normalized to the height of the peak of the internal standard is plotted versus the target oligonucleotide. Therefore, in this dynamic range of target oligonucleotide concentration, any detector response can be quantitated and correlated to a target oligonucleotide. The correlation coefficient is $R^2=0.99$.

Thus, these results demonstrate that the method of the invention provides a working protocol for the quantitative analysis of sub ppb levels of a target oligonucleotide in complex biological fluid samples.

The following examples illustrate the preferred modes of making and practicing the present invention, but are not meant to limit the scope of the invention since alternative methods may be utilized to obtain similar results.

EXAMPLES

1. Chemicals and Reagents

Ultra-pure Tris base, urea, acrylamide, and EDTA were obtained from Schwartz/Mann Biotech (Cleveland, Ohio). N, N, $N^1$, $N^1$- (tetramethylethyl-enediamine (TEMED) and ammonium persulfate were obtained from Bio-Rad (Richmond, Calif.). Boric acid was obtained from Sigma (St. Louis, Mo.). All oligonucleotide analogs were synthesized by known methods (Uhlmann et al. *Analyt. Chem.* (1990) 90: 543–583) desalted, lyophilized, and reconstituted in sterile water for injection (Lyphomed Deerfield, Ill.).

2. Preparation and Labelling of Primer Oligonucleotide and Preparation of Helper Oligonucleotide The primer and helper oligonucleotides were synthesized by the phosphoramidite method (see McBride et al. (1983) *Tetrahedron Lett.* 24: 245) using an Oligo 100™ automated DNA synthesizer (Beckman, Fullerton, Calif.). Derivatized fluorescein ("FAM") was covalently attached to the 5' end of the primer by phosphoramidite chemistry using an automated oligonucleotide synthesizer.

3. Preparation of Gel Filled Capillaries for HPCE

Fused-silica capillary tubing (Polymicro Technologies, Phoenix, Ariz.) with an inner diameter of 75 μm, an outer diameter of 375 μm, an effective length of 15–20 cm, and a total length of 30–60 cm is treated with (methylacryloxypropyl) trimethoxysilane (Petrarch Systems, Bristol, Pa.) and then filled with a degassed solution of polymerizing acrylamide in aqueous or organic solvent (e.g. formamide) media including 0.1–0.3M Tris-borate, 2–6 mM EDTA TBE buffer, pH 8.3, containing 6M to 8.3M urea). Polymerization was achieved by adding ammonium persulfate solution and TEMED.

4. Hybridization of Primer and Helper to Target Oligonucleotide 100 ppb of fluorescently labelled 13 mer primer and 500 ppb of 12 mer (SEQ ID NO:3) or 33 mer (SEQ ID NO:2) helper are mixed in the presence of target oligonucleotide analog (SEQ ID NO:1). The mixture is incubated at 37° C. for 15 min and then cooled to 4° C. for 15 minutes.

5. Ligation

In the ligation step, 40 units T4-DNA ligase is added and incubated at 37° C. for 60 minutes in the presence of 500 mM Tris, 100 mM $MgCl_2$, 100 mM DTT, 100 mM ATP, and 15 μg/ml BSA (U.S. Biolabs, Cleveland, Ohio). Final volume is 15 μl.

6. Separation and Detection Methods

Separation is accomplished using gel HPCE and quantitative detection by either UV or LIF. The capillary electrophoresis apparatus with UV and laser-induced fluorescence detection capability and the preparation of gel-filled capillaries for the separation of DNA molecules are essentially as described by Cohen et al. (*J. Chromatogr.* (1990) 516: 49–60), herein incorporated herein by reference. A 30 kV, 500 μA, direct current high voltage power supply (Model ER/DM; Glassman, Whitehouse Station, N.J.) is used to generate the potential across the capillary.

UV detection of oligonucleotide analogs at 270 nm is accomplished with a Spectra 100 (Spectra-Physics, San Jose, Calif.).

For LIF detection, an argon ion laser (Model 543 100BS or Model 532 AT, Omnichrom, Chino, Calif.) is employed. The laser is mounted on a 4×6 foot optical table (Model 10531/13825, Oriel, Stamford, Conn.), and operated in the light-regulated mode at 0.03–0.05 W. The laser light was passed through a narrow band filter (Model D1-488, Corion, Holliston, Mass.), directed by reflection using a beam steerer (Model M670, Newport) and focused into the capillary with a 25-mm focal length lens (Model KBX043, Newport). Fluorescence from the sample is collected with a 40×microscope objection (Model M-Set, Newport) and passed through an interference filter (Model S10-520-R, Corion) and a colored glass filter (Model OG520, Schott Glass Technol., Duryea, Pa.). A Photomultiplier tube (Model R928, Hamamatzu, San Jose, Calif.) operated at 700 V and a photomultiplier readout (Model 7070, Oriel) are used to detect fluorescence. The resulting voltage output is displayed on a strip chart recorder and is simultaneously transmitted to an analog-to-digital (A/D) interface (Model 760 SB, Nelson Analytical, Cupertino, Calif.) for transfer to a PC (Model ZBF-2526-EK, Zenith Data Systems). The data are acquired and stored on an AcerPower 486/33 computer (Acer American Corp., San Jose, Calif.) through an analog-to-digital converter (Model 970, Nelson Analytical Cupertino, Calif.).

7. Solid Phase Extraction

AX-Nucleobond Cartridges (20AX) (Bodman, Aston, Pa.) are equilibrated with Buffer I (100 mM Tris-$H_3PO_4$, pH 6.3, 0.5M KCl, 15% ethanol). Nucleic acids in serum samples are then adsorbed from the serum by mixing 1 ml of serum with 0.4 ml Buffer 2 (100 mM Tris-$H_3PO_4$, pH 6.3, 1M KCl, 15% ethanol). The oligonucleotides so obtained are washed from the cartridges with 800 μl of Buffer 3 (25 mM Tris-$H_3PO_4$, pH 7, 2M LiBr). After extraction, 8 μl of each sample is taken for ligation with the labelled 13-mer primer oligonucleotide analog as described above. Then, 10 μl ligation solution is applied to a dialysis filter (Millipore, Bedford, Mass.) for about 60 minutes to reduce the concentration of ions in the solution. The resulting sample is mixed with a labelled internal standard (e.g., a fluorescein-labelled 25 mer oligonucleotide whose final concentration, 5 ppb) and injected into the capillary gel electrophoresis system. The substrate in the capillary includes 12% T acrylamide, 33% (volume:volume) formamide, 7M urea, and 2×TBE. The length of the capillary is 10 cm, and E=400 v/cm.

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A method of detecting amounts of less than twenty parts per billion of a single-stranded target oligonucleotide in a biological fluid without amplifying or immobilizing the target oligonucleotide, comprising the steps of:

(a) providing a primer and a helper,
the primer being a single-stranded oligonucleotide consisting of at least four covalently linked nucleotides, and a fluorescent label covalently linked to at least one of the primer nucleotides, and
the helper being a single-stranded oligonucleotide comprising at least three covalently linked nucleotides;

(b) contacting a biological fluid sample to-be-tested with the primer and the helper under conditions conducive for the annealing of the primer and the helper to a complementary, single-stranded oligonucleotide, a labelled, double-stranded molecule being formed if the sample contains the single-stranded target oligonucleotide, the target oligonucleotide having a nucleotide sequence complementary to the nucleotide sequences of the primer and the helper oligonucleotides;

(c) ligating the annealed primer and the annealed helper, thereby forming a labelled, single-stranded ligation product annealed to the target molecule;

(d) separating the ligation product from the primer, helper, and target oligonucleotides by high performance capillary gel electrophoresis to produce a labeled electrophoretic peak corresponding to the ligation product; and (e) normalizing the labeled electrophoretic peak to an internal standard peak corresponding to a known amount of oligonucleotide, thereby quantitating the ligation product.

2. The method of claim 1 wherein the target oligonucleotide is an oligonucleotide analog.

3. The method of claim 2 wherein the target oligonucleotide is an oligonucleotide analog comprising nucleotides selected from the group consisting of ribonucleotides, deoxyribonucleotides, modified ribonucleotides, modified deoxyribonucleotides, and mixtures thereof.

4. The method of claim 1 wherein the helper consists of from 3 to 100 nucleotides.

5. The method of claim 1 wherein the fluorescent label on the primer oligonucleotide is excitable in the UV or visible range and fluoresces in the visible range.

6. The method of claim 1 wherein the biological fluid to-be-tested is selected from the group consisting of plasma, serum, urine, saliva, sweat, cerebrospinal fluid, synovial fluid, lacrimal secretions, seminal fluid, and cell and tissue extracts.

7. The method of claim 1 wherein the primer consists of at least eight covalently linked oligonucleotides.

8. The method of claim 1 wherein contacting step (b) is carried out at from about 4° C. to 90° C. in the presence of from about 0.05M to 2.0M salt, the salt comprising an alkali metal or an alkaline earth metal.

9. The method of claim 1 wherein the contacting step comprises contacting about 100 parts primer and 100 parts helper with about 1 to 10 parts target oligonucleotide.

10. The method of claim 1 wherein ligating step (c) comprises ligating the primer to the helper with an enzyme selected from the group consisting of T4-DNA ligase, Taq DNA ligase, and *E. coli* DNA ligase.

11. The method of claim 1 wherein detecting step (d) comprises detecting the labelled ligation product by UV absorption or laser-induced fluorescence.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

CTCTCGCACC CATCTCTCTC CTTCT       25

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO -continued (iv) ANTI-SENSE: YES (xi) SEQUENCE DESCRIPTION: SEQ ID NO:2:

AGAAGGAGAG AGA 13

(2) INFORMATION FOR SEQ ID NO:3:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

TGGGTGCGAG AG 12

(2) INFORMATION FOR SEQ ID NO:4:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

TGGGTGCGAG AGTTTTTTTT TTTTTTTTT TTT 33

(2) INFORMATION FOR SEQ ID NO:5:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

AGAAGGAGAG AGATGGGTGC GAGAGTTTTT TTTTTTTTT TTTTT 46